United States Patent [19]

Heinrich et al.

[11] Patent Number: 5,703,010
[45] Date of Patent: Dec. 30, 1997

[54] FORMULATIONS OF CROP PROTECTION AGENTS

[75] Inventors: Rudolf Heinrich, Kelkeim; Thomas Maier, Frankfurt am Main; Jean Kocur, Hofheim am Taunus; Rainer Schlicht, Bad Camberg, all of Germany

[73] Assignee: Hoechst Aktiengesellschaft, Frankfurt, Germany

[21] Appl. No.: 711,874

[22] Filed: Sep. 12, 1996

Related U.S. Application Data

[62] Division of Ser. No. 404,940, Mar. 15, 1995, Pat. No. 5,602,177, which is a continuation of Ser. No. 830,644, Feb. 4, 1992, abandoned.

[30] Foreign Application Priority Data

Feb. 6, 1991 [DE] Germany ............ 41 03 467.8
Aug. 22, 1991 [DE] Germany ............ 41 27 757.0

[51] Int. Cl.⁶ ............ A01N 25/12; A01N 43/76; A01N 53/10
[52] U.S. Cl. ............ 504/116; 504/139; 504/231; 504/270; 504/272; 424/408; 514/431; 514/952; 514/962
[58] Field of Search ............ 504/116, 139, 504/231, 270, 272; 514/431, 952, 962; 424/408

[56] References Cited

U.S. PATENT DOCUMENTS

| | | | |
|---|---|---|---|
| 3,920,442 | 11/1975 | Albert et al. | 71/92 |
| 4,310,520 | 1/1982 | Narazaki et al. | 424/200 |
| 4,400,196 | 8/1983 | Albrecht et al. | 71/86 |
| 5,178,872 | 1/1993 | Ohtsubo et al. | 424/408 |

FOREIGN PATENT DOCUMENTS

| | | |
|---|---|---|
| 2 290 844 | 6/1976 | France. |
| 2 398 455 | 2/1979 | France. |
| 2 645 709 | 10/1990 | France. |
| 1 542 902 | 4/1970 | Germany. |
| 60-036402 | 2/1985 | Japan. |
| 2-108604 | 4/1990 | Japan. |
| 2 013 610 | 8/1979 | United Kingdom. |
| 2 230 700 | 10/1990 | United Kingdom. |

OTHER PUBLICATIONS

Bakan, J.A. et al., "Microencapsulation", in Leon Lachman et al. *The Theory and Practice of Industrial Pharmacy*, 2nd Ed. 1976.

Ullmann's *Encyclopedia of Industrial Chemistry*, 5th Ed., pp. 585–587 (1990).

*Primary Examiner*—S. Mark Clardy
*Attorney, Agent, or Firm*—Curtis Morris & Safford, P.C.

[57] ABSTRACT

The invention relates to water-emulsifiable granules of crop protection agents composed of the pesticidal active substance in liquid or dissolved form and an at least partially water-soluble shell-forming structural material, to the use of these granules as novel, advantageous formulations of crop protection agents, and to processes for their preparation. It furthermore relates to the general use of polyvinyl alcohols as shell-forming structural materials in the preparation of water-emulsifiable granules which contain organic compounds dissolved in a high-boiling solvent or solvent mixture.

7 Claims, No Drawings

FORMULATIONS OF CROP PROTECTION AGENTS

This application is a division of application Ser. No. 08/404,940, now U.S. Pat. No. 5,602,177, filed Mar. 15, 1995, which is a continuation of application Ser. No. 07/830,644, filed on Feb. 4, 1992 (now abandoned).

The invention relates to water-emulsifiable granules of crop protection agents composed of the active substance in liquid or dissolved form and of an at least partially water-soluble shell-forming structural material, to the use of these granules as novel, advantageous formulations of crop protection agents, and to processes for their preparation.

Crop protection agents are preferably commercially available in the form of emulsifiable concentrates (EC), concentrated emulsions (EW), aqueous dispersions (SC) and wettable powders (WP).

To prepare spray mixtures, the agents are introduced into water and applied, for example with stirring. Each of these types of preparations has advantages and disadvantages and must be designed to suit, inter alia, the physical and chemical properties of the active substance, an optimum biological effect, toxicological requirements as well as safe handling by the user.

Wettable powders for example result in the troublesome development of dust during the preparation and the application and also have the disadvantage of poor volumetric metering prior to application. Emulsifiable concentrates contain aromatic solvents which can be highly flammable, irritating to the skin or have an unpleasant odor.

Dispersions, when stored over prolonged periods, can give rise to sediments which are difficult to shake up. Only active substances capable of being ground can be made into dispersions. This formulation type furthermore frequently presents problems relating to the disposal of the packaging materials.

Most of these disadvantages can be overcome by using a novel type of formulation, water-dispersible granules (WG). These formulations are free-flowing and low-dust and can readily be metered volumetrically. They can be packaged without problems in polyethylene containers, cardboard drums or gusseted bags made of composite films, can be emptied easily after application and therefore disposed of more readily, also with regard to the packaging volume to be disposed of.

A large number of processes can be used for preparing water-dispersible granules industrially (cf. H. B. Ries "Granuliertechnik und Granuliergeräte" [Granulation Technology and Granulation Equipment] in Aufbereitungstechnik No. 3, 1970, p. 147, and M. Rosch and R. Probst in Verfahrenstechnik 9 (1975), p. 59 to 64).

In particular, it is known to prepare water-dispersible granules by the fluidized bed technique which can be operated in countercurrent and in cocurrent flow.

U.S. Pat. No. 3,920,442 and GB-A-1 4,013,904 as well as M. Rosch and R. Probst in Verfahrenstechnik 9 (1975), p. 59, describe the countercurrent process, while EP-A-26,918, EP-A-141,436 and EP-A-1,441,437 as well as Verfahrenstechnik 9 (1975), p. 61, 62, describe the cocurrent flow method. To guarantee application without problems, water-dispersible granules must have good wettability when introduced into water, disintegrate as spontaneously as possible and form a good suspension having good stability.

DE-A-4,013,028 describes emulsifiable solid pesticidal agents in granule form which contain dextrin and/or lactose and their preparation in a two-stage process (spray-drying and granulation).

However, the most important prerequisite for the applicability of water-dispersible granules in practice is a sufficiently high biological activity, and, to optimize the latter, such an amount of wetting agent is generally added that the wetting agent concentrations in the spray mixtures during application are 0.2 to 0.4% by weight. In the case of selective herbicides, excessive amounts of wetting agent can result in phytotoxic symptoms on crop plants, and insufficient amounts of wetting agent can result in an insufficient action. Moreover, foam formation may be excessively high when too large an amount of wetting agent is used in the spray mixture, and this foam formation can interfere with the application process and cannot be prevented even by adding antifoam agents.

It is known from EP-A-224,845 that herbicidal active substances can be formulated as so-called water-suspendable granules (WG), thus avoiding the disadvantages which occur when wettable powders are used, such as troublesome development of dust prior to application. However, it has emerged that these water-suspendable granules do not always unfold the optimum biological action, caused by the effect of the solvent on the penetration of the active substance through the leaf surface, or, alternatively, that the crop plants are damaged by excessive amounts of wetting agent. The above-described difficulties caused by troublesome development of foam also arose in most cases.

DE-A-2,805,106 furthermore describes how, in a spray tower, liquid, water-insoluble filling material is encapsulated in microcapsule powder of capsule diameter 1 to 20 μm with the aid of water-soluble polyvinyl alcohols.

GB Patent 1,305,369 furthermore discloses the coating of vegetable oils with water-soluble polymers such as polyvinyl alcohol or polyvinylpyrrolidone by spray-drying, giving microcapsules of capsule diameter 0.6 μm.

However, the two last-mentioned processes only result in very small microparticles having the advantages already mentioned above, namely troublesome dust problems and poor volumetric metering.

It was therefore an object to prepare water-emulsifiable granules which overcome all the abovementioned disadvantages and which lead to a free-flowing, non-dusting, water-emulsifiable product which can readily be metered volumetrically. Moreover, this product must be wetted thoroughly when introduced into water and must dissolve as spontaneously as possible and form a stable emulsion with good properties in use.

The object is achieved for example by emulsifiable solid granules based on milk powder containing the active substance, if appropriate as a solution in an organic solvent, and, if appropriate, further additives or adjuvants.

However, the object is achieved much more advantageously by coating the active substances with a substantially inert, film-forming substance which dissolves sufficiently rapidly in water. For example, various polyvinyl alcohol types corresponded to the requirements to be met. Equally suitable are natural, or semisynthetic, polymers such as gelatin, gum arabic, low-molecular-weight starch derivatives (hydrolyzates), sodium alginates, cellulose derivatives (low-molecular-weight ®Tyloses) such as hydroxymethylcellulose and synthetic polymers such as the polyvinyl alcohols and polyvinylpyrrolidones which have already been mentioned, and mixtures of the substances which have been listed; polyvinyl alcohols are preferred. From amongst these materials, in particular the polyvinyl alcohol types which are known, the expert can select those which have optimum properties as regards film-forming capacity and solubility in water, and, on the other hand, do not interfere while the active substances are being coated.

Surprisingly, it has now been found that the use of the water-soluble substances which have been listed, in particular certain polyvinyl alcohol types or mixtures of these, allows water-emulsifiable granules of an average particle diameter of 0.3 to 5 mm, preferably 0.5 to 2 mm, to be obtained by the above-described fluidized bed process, operated in countercurrent, which are dust-free, free-flowing, readily emulsifiable in water and can readily be metered volumetrically.

This fact is surprising in so far as it could not have been anticipated that the desired granules are formed in the above-mentioned experimental set-up, while the set-up described in DE-A-2,805,106 and the experiments described in GB Patent 1,305,369 gave particles of a size of 0.5 and 0.6 to 20 μm, respectively. Moreover, it was surprising that the resulting water-emulsifiable granules exhibited the same biological action, or, in some cases, even a slightly better biological action, than the corresponding emulsifiable concentrates.

The invention therefore relates to water-emulsifiable granules which contain a) 2 to 70% by weight, preferably 10 to 40% by weight, of at least one pesticidal active substance which is not, or only sparingly, soluble in water, b) 0 to 80% by weight, preferably 20 to 60% by weight, of a high-boiling solvent or solvent mixture, preferably selected from the group comprising the polycyclic aromatic compounds, c) 10 to 80% by weight, preferably 30 to 60% by weight, of an at least partially water-soluble shell-forming structural material, d) 0 to 40% by weight, preferably 0 to 20% by weight, of one or more wetting agents preferably selected from the group comprising the alkanesulfonates, alkylnaphthalenesulfonates, alkylbenzenesulfonates, alkyl polyglycol ether sulfonates, alkylsulfosuccinic monoesters and fatty acid N-methyltaurides, or mixtures of the above wetting agents, e) 0 to 20% by weight, preferably 5 to 15% by weight, of conventional formulation auxiliaries selected from the group comprising the fillers, penetrants, adhesives and antifoam agents.

An addition of finely-ground solid active substances also makes it possible to combine the principle of water-emulsifiable granules with that of water-dispersible granules. The invention therefore also relates to granules which contain, besides the above-described principle, further active substances in solid, finely distributed form. This method can be particularly useful when an active substance which is only sparingly soluble in organic solvents is to be combined with an active substance for whose optimum biological action an aromatic solvent is required, or is advantageous, as penetrant.

A further, particular advantage of this process is the fact that it is now possible to combine active substances which are not miscible with each other, or which interfere with each other. For example, various active substances which would alter each other, or which would be altered by external factors, for example due to hydrolysis or oxidation, can be combined without problems.

To date, combinations of active substances which were incompatible with each other could frequently not be realized at all or had to be stored separately and then prepared immediately prior to application, for example by mixing in the spray tank in the case of crop protection agents.

In general, the active substances which can be used for these preparations include those which, due to their low melting point, can only be converted with difficulty, or not at all, into a finely-disperse aqueous phase with the aid of grinding apparatus, or, alternatively, those active substances for which the grinding process requires particular safety measures.

Suitable pesticidal active substances to be employed are herbicides and safeners, insecticides, fungicides, acaricides, nematicides, pheromones or repellents, these substances being not, or only sparingly, soluble in water. However, solid active substances should be readily soluble, or very readily soluble, in one of the organic solvents mentioned below.

Suitable herbicides are, in particular, leaf-acting herbicides which unfold their biological potential mainly, or do so better, in dissolved form, but which are intended to be used in the form of solid formulations. Examples of suitable herbicidal active substances are alkyl phenoxyphenoxy- or hetaryloxyphenoxypropionates such as methyl α-4-(2',4'-dichlorophenoxy)phenoxypropionate [common name: diclofop-methyl] (A), ethyl 2-[4-(6-chloro-2-benzothiazolyloxy)phenoxy]propionate (B) or ethyl 2-[4-(6-chloro-2-benzoxazolyloxy)phenoxy]propionate (common name: fenoxaprop-P-ethyl) (C), a dinitroaniline compound such as 2,6-dinitro-4-trifluoromethyl-N,N-dipropylaniline [common name: trifluralin] (D) or 2,6-dinitro-4-isopropyl-N,N-dipropylaniline [common name: isopropalin] (E), hydroxybenzonitrile derivatives such as 2,6-dibromo-4-hydroxybenzonitrilooctanoate (F), dinitrophenol compounds such as 2-sec.butyl-4,6-dinitrophenol [common name: dinoterb] (G).

Examples of suitable safeners are the compounds described in EP-A-86,750, EP-A-94,349, EP-A-191,736, EP-A-346,620, EP-A-333,131, EP-A-269,806, EP-A-159,290, DE-A-2,546,845, PCT/EP-90/02,020 and PCT/EP-90/01,966.

Examples of suitable insecticides are 1,4,5,6,7,7-hexachloro-8,9,10-trinorborn-5-ene-2,3-ylenedimethyl sulfite [common name: endosulfane], 2-(1-methyl-n-propyl)-4,6-dinitrophenyl 3-methylcrotonate [common name: binapacryl], phosphates such as O,O-diethyl O-1-phenyl-1H-1,2,4-triazol-3-ylphosphorothioate [common name: triazophos], or pyrethroids such as (S)-α-cyano-3-phenoxybenzyl (1R,3R)-3-(2,2-dibromovinyl)-2,2-dimethylcyclopropanecarboxylate [common name: deltamethrin], acrinathrin, allethrin, alphamethrin, bioallethrin, ((S)-cyclopentenyl isomer), bioresmethrin, cycloprothrin, cyfluthrin, cyhalothrin, cypermethrin, α-cyano-3-phenyl-2-methylbenzyl 2,2-dimethyl-3-(2-chloro-2-trifluoromethylvinyl)-cyclopropanecarboxylate (FMC 54800), fenpropathrin, fenfluthrin, flumethrin, permethrin, resmethrin or tralomethrin. Preferred pyrethroids are acrinathrin, tralomethrin, bioresmethrin, permethrin and cypermethrin; deltamethrtn is particularly preferred.

Another insecticide which is suitable is (4-ethoxyphenyl)-[3-(4-fluoro-3-phenoxyphenyl)propyl]dimethylsilane (silafluofen).

The pyrethroids listed are known, for example, from GB Patents 1,413,491, 1,168,797, 1,168,798 and 1,168,799, FR Patent 2,364,884 or EP-A-48,186. So-called synergists, such as piperonyl butoxide, sesamex, sesame seed oil, sulfoxide, MGK or octachlorodipropyl ether, can be admixed to the pyrethroids.

A suitable fungicide which may be mentioned is, for example, ethyl 2-diethoxythiophosphoryloxy-5-methylpyrazolo[1,5 a]pyrimidine-6-carboxylate [common name: pyrazophos] and, furthermore, a suitable pheromone the compound (E)-8-(E)-10-dodecadienol or (Z)-7,8-epoxy-2-methyloctadecane and a suitable repellent is dimethyl phthalate.

The abovementioned herbicides (with the exception of compound (B)), insecticides, and the repellent, are known from H. Martin, Pesticide Manual 6th edition 1979. Herbicides (B) and (C) are described in DE-A-2,640,730, and the two pheromones are described in M. Beroza, Chem. Controlling Insect Behaviour, Academic Press, N.Y. 1970.

Preferred dispersing agents which can optionally additionally be used are lignosulfonates, sodium salts of dinaphthylmethanedisulfonic acids, the sodium salt of a sulfonic acid made from cresol, formaldehyde, sodium sulfite and oxynaphthalenesulfonic acid, the sodium salt of a sulfonic acid made from m-cresol, formaldehyde and sodium sulfite, condensation products of arylsulfonic acids and sodium salts of formaldehyde, as well as triethanolamine salts of phosphorylated polystyrylphenylpolyethylene oxides, polyvinyl alcohol, calcium dodecylbenzenesulfonate, and also alkylnaphthalenesulfonates of various alkyl chain lengths.

Emulsifiers which can optionally additionally be added are nonionic, anionic or cationic surface-active substances, and mixtures of nonionic with anionic components are preferably used. However, combinations of nonionic and cationic surface-active agents can also be used. The emulsifiers which are preferably employed include calcium phenylsulfonate, ethoxylated nonylphenols, ethoxylated aliphatic alcohols, ethoxylated castor oil, fatty acid polyglycol esters, propylene glycol/ethylene glycol block polymers and mixtures of these, as well as phosphorylated ethylene glycol/propylene glycol/ethylene glycol block polymers.

Organic solvents which are suitable are mainly high-boiling aromatic substances, for example 1- or 2-methylnaphthalene, dimethylnaphthalenes or other polycyclic aromatic substances. However, other solvents which are not miscible with water are also suitable, for example aromatic substances such as alkylbenzenes, xylenes, aliphatic substances such as paraffin oils, vegetable oils, alicyclic substances, alkanols such as cyclohexanol, isooctyl alcohol, ethers, ketones such as cyclohexanone, 4-methylcyclohexanone, isophorone, esters such as ethyl benzoate and tri-n-butyl phosphate. Liquid pesticidal active substances can also be used without organic solvents.

The preferred shell-forming structural materials are polyvinyl alcohols obtained by hydrolysis, preferably partial hydrolysis of polyvinyl acetate, or mixtures of these polyvinyl alcohols having a degree of hydrolysis of preferably 72 to 99 mol % and a viscosity of preferably 2 to 18 cP[1] measured in a 4% strength aqueous solution at 20° C. (for example ®Mowiol types). The polyvinyl alcohols which are preferred for the present invention have a molecular weight of preferably 10,000 to 200,000. They are prepared by partial, preferably 72 to 99 mol %, alkaline hydrolysis of suitable polyvinyl acetates.

[1] 1cP=1 mPa.s

To carry out the process in practice, the aqueous phase (carrier phase) is first prepared by stirring the shell-forming structural material (for example polyvinyl alcohol) and the wetting of dispersing agent into water. The active substance to be emulsified is then dissolved in the solvent, and the solution is dispersed in the aqueous phase with moderate stirring. It is possible to add additional formulation adjuvants or finely-ground solid active substances during this procedure.

Dispersing can be effected by stirring or, if appropriate, also by a shaking procedure, using generally customary technical equipment. This includes, for example, stirred vessels with high-speed stirrer, or, alternatively, tube-shaped reactors which are equipped with suitable stirring devices. The addition can be effected batchwise or continuously if suitable apparatuses are used. The temperature can be kept constant during the dispersing procedure, but it can also be varied after certain periods. It should expediently be in the range from 10° to 80° C., preferably 20° to 50° C.

Such a procedure allows a dispersion of the water-insoluble phase to be produced in the aqueous polyvinyl alcohol solution in which the droplets formed have a diameter of 1 to 20 µm, preferably 5 to 10 µm, depending on the speed of stirring or dispersing.

When the dispersion is stirred, troublesome foam formation may occasionally occur. However, this can be substantially suppressed by adding a suitable antifoam agent, for example triisobutyl phosphate, a defoamer SF or silicone defoamer.

If it is desirable and expedient to establish a certain pH, then this adjustment can be effected before, during or even after the dispersing procedure. However, in most cases such an additional measure can be dispensed with.

The water-dispersible granules according to the invention are prepared industrially for example in such a way that the resulting viscous dispersion (emulsion, suspension or suspoemulsion) is continuously fed to a fluidized bed drier by the countercurrent principle, thus removing the water from the product in a stream of warm air. To avoid potential problems such as stringiness, film formation on the walls of the drying unit, clogging of the inlet opening and formation of larger agglomerates, the viscosity of the initial product used should be between 50 and 5000 cp, preferably between 100 and 1000 cp, depending on the metering conditions and drying temperatures selected.

However, it must be taken into account that the resolubility of the PVA film can be markedly reduced by too intense a heat treatment. This is why, in the case of PVA, feed temperatures of 100° C. to 150° C. and discharge temperatures of 40° to 60° C. are preferred, and care is taken that the dried, finished granules are not subjected to prolonged thermal stress on the walls of the drying unit. The abovementioned drying process allows water to be removed from the granules down to a residual moisture content of less than 0.5% by weight.

The resulting granules have an average particle size of 0.3 to 5 mm, preferably 0.5 to 2 mm, are free-flowing, do not evolve dust, can readily be metered volumetrically, and form a stable emulsion in water. The filler is present in amounts of 10 to 90% by weight, preferably 30 to 75% by weight.

It can be demonstrated that the properties of the products according to the invention are essentially unchanged after 3 months' storage at room temperature or at 50° C.

Surprisingly, the process according to the invention even allows those active substances for which known methods present problems in the formulation of stable emulsion concentrates, or do not allow such a formulation at all, to be converted into emulsifiable granules which are easy to manipulate, can be solvated within a few minutes by a simple dispersion process in water in order to apply the active substance in practice, and can form highly stable ready-to-use emulsions, where, surprisingly, the aqueous solution of polyvinyl alcohol, which has been used as the shell-forming structural material, simultaneously acts as the wetting and dispersing agent, or emulsifier, and no additional emulsifiers are required in some cases. The at least partially water-soluble shell-forming structural materials, in particular polyvinyl alcohol, additionally act as an adhesion promoter when the emulsions which have been prepared with the granules according to the invention are applied to the plant.

However, it is also possible in each individual case to formulate the water-emulsifiable granules according to the invention even more application-specifically by adding further wetting agents, dispersants and/or emulsifiers.

This means that the process according to the invention is particularly suitable for formulating active substances for use in the field of crop protection and pest control, and also for the field of chemical technology.

The invention therefore also relates to the general use of at least one polyvinyl alcohol obtained by partial hydrolysis of polyvinyl acetate, in an amount of 10 to 80% by weight, as shell-forming structural material in the preparation of water-emulsifiable granules containing 2 to 70% by weight, preferably 10 to 40% by weight, of at least one organic compound which is dissolved in a high-boiling solvent or solvent mixture.

This means that, according to the invention, suitable pesticidal active substances for these processes are, for example in particular all those which are liquid or are soluble in an organic solvent, which are immiscible with water, or whose solutions are immiscible with water, and whose boiling points are above the boiling point of water.

The process is illustrated by the examples below without imposing any restrictions on the invention:

EXAMPLE 1

100 g of a polyvinyl alcohol which has been prepared by partial hydrolysis of polyvinyl acetate and which has a viscosity of 3 cP (measured in a 4% strength aqueous solution at 20° C.) and a degree of hydrolysis of 83 mol % are dissolved in 500 g of water, and 50 g of a polyvinyl alcohol which has been prepared in the same manner and which has a viscosity of 4 cP and a degree of hydrolysis of 88 mol % are slowly added with vigorous stirring.

A solution of 90 g of fenoxaprop-P-ethyl in 260 g of methylnaphthalene is run into this aqueous phase with further stirring, and the speed of the stirrer is then increased to such an extent that the droplets which form in the aqueous phase reach an average diameter of 5 to 10 μm.

The dispersion is then injected into a laboratory fluidized bed drier. The resulting water-emulsifiable granules have a particle diameter of 0.5 to 2 mm, do not evolve dust, are free-flowing, can readily be metered volumetrically and can be emulsified readily in water.

EXAMPLE 2

8 kg of a polyvinyl alcohol which has been prepared by partial hydrolysis of polyvinyl acetate and which has a viscosity of 3 cP (measured in a 4% strength aqueous solution at 20° C.) and a degree of hydrolysis of 83 mol % are dissolved in 30 kg of water, and 1.5 kg of sodium alkyl biglycol ether sulfate are added with vigorous stirring. When the salt is dissolved, solutions of 3 kg of fenoxaprop-ethyl and 1.5 kg of fenchlorazole in 14 kg of methylnaphthalene are run in, and the mixture is stirred until the droplets which form in the aqueous phase reach an average diameter of 5–10 μm.

The dispersion is then injected into a fluidized bed drier which is suitable for these amounts of product. The resulting water-emulsifiable granules have a particle diameter of 0.5 to 2.0 mm, do not evolve dust, are free-flowing, can readily be metered volumetrically and form a stable emulsion in water.

EXAMPLE 3

100 g of a polyvinyl alcohol which has been prepared by partial hydrolysis of polyvinyl acetate and which has a viscosity of 3 cP (measured in a 4% strength aqueous solution at 20° C.) and a degree of hydrolysis of 83 mol % are dissolved in 600 g of water, and 50 g of a polyvinyl alcohol which has been prepared in the same manner and has a viscosity of 4 cP and a degree of hydrolysis of 88 mol % are slowly added with vigorous stirring. 20 g of 1.0 a sulfonylurea herbicide DPXL 5300, which has previously been ground in a bead mill to a particle size of 1–5 μm, are then added, and the aqueous phase is homogenized. A solution of 60 g of fenoxaprop-P-ethyl and 30 g of fenchlorazole in 260 g of methylnaphthalene is then run into this aqueous phase while continuing stirring, and the speed of the stirrer is then increased so that the oily droplets which form in the aqueous phase have an average diameter of 5–10 μm.

The resulting suspoemulsion is then injected into a laboratory fluidized bed drier. The resulting water-dispersible granules have a particle diameter of 0.5–2 mm, have the abovementioned good technical properties in use and form a stable suspoemulsion in water.

EXAMPLE 4

100 g of a polyvinyl alcohol which has been prepared by partial hydrolysis of polyvinyl acetate and which has a viscosity of 3 cP (measured in a 4% strength aqueous solution at 20° C.) and a degree of hydrolysis of 83 mol % are dissolved in 500 g of water, and 50 g of a polyvinyl alcohol which has been prepared in the same manner and has a viscosity of 4 cP and a degree of hydrolysis of 88 mol % are slowly added, with vigorous stirring.

A solution of 20 g of endosulfane in 30 g of methylnaphthalene is run into this aqueous phase, and the speed of the stirrer is then increased so that the oily droplets which form in the aqueous phase have an average diameter of 5–10 μm.

The dispersion is then injected into a laboratory fluidized bed drier. The resulting water-emulsifiable granules have a particle diameter of 0.5–2 mm, have the abovementioned good technical properties in use and form a stable emulsion in water.

EXAMPLE 5

100 g of a polyvinyl alcohol which has been prepared by partial hydrolysis of polyvinyl acetate and has a viscosity of 3 cP (measured in a 4% strength aqueous solution at 20° C.) and a degree of hydrolysis of 83 mol % are dissolved in 600 g of water. 60 g of a polyvinyl alcohol which has been prepared in the same manner and which has a viscosity of 4 cP and a degree of hydrolysis of 88 mol % are slowly added with vigorous stirring.

A solution of 21 g of deltamethrin in 219 g of methylnaphthalene is run into this aqueous phase while continuing stirring, and the speed of the stirrer is then increased to such an extent that the droplets which form in the aqueous phase reach an average diameter of 5 to 10 μm.

The dispersion is then dried in a laboratory fluidized bed drier to give water-emulsifiable granules which have a particle diameter of 0.5 to 2 mm and the abovementioned good technical properties in use. A stable emulsion is formed when the granules are introduced into water.

EXAMPLE 6

100 g of a polyvinyl alcohol which has been prepared by partial hydrolysis of polyvinyl acetate and which has a viscosity of 3 cP (measured in a 4% strength aqueous solution at 20° C.) and a degree of hydrolysis of 83 mol % are dissolved in 600 g of water. 60 g of a polyvinyl alcohol which has been prepared in the same manner and which has a viscosity of 4 cP and a degree of hydrolysis of 88 mol % are slowly added with vigorous stirring.

A solution of 50 g of silafluofen in 190 g of methylnaphthalene is run into this aqueous phase while continuing stirring, and the speed of the stirrer is then increased to such an extent that the droplets which form in the aqueous phase reach an average diameter of 5 to 10 µm.

The dispersion is then granulated in a laboratory fluidized bed drier. The granules have a particle diameter of 0.5–2 mm and the abovementioned good technical properties in use and form a stable emulsion when introduced into water.

We claim:

1. Water-emulsifiable granules having an average particle diameter of 0.3 to 5 mm, which granules comprise
   - 2 to 70% by weight of a pesticidally active substance which is not soluble, or which is only sparingly soluble in water, selected from the group consisting of herbicides, safeners, insecticides, fungicides, acaricides, nematicides, pheromones and repellants,
   - 20 to 80% by weight of a high-boiling solvent or solvent mixture, and
   - 10 to 80% by weight of an at least partially water-soluble shell-forming structural material, which shell-forming structural material is comprised of a polyvinyl alcohol obtained by partial hydrolysis of polyvinyl acetate, or of a mixture of such polyvinyl alcohols, and which granules do not contain deltamethrin as the pesticidally active substance.

2. The granules as claimed in claim 1, which further comprise
   - 0 to 20% by weight of one or more wetting agents, and
   - 0 to 20% by weight of customary formulation adjuvants.

3. The granules as claimed in claim 1, wherein the active substance is selected from the group consisting of pyrethoid insecticides.

4. Water-emulsifiable granules having an average particle diameter of 0.3 to 5 mm, which granules comprise
   - 2 to 70% by weight of fenoxaprop-ethyl, and
   - 10 to 80% by weight of an at least partially water-soluble shell-forming structural material, which shell-forming structural material is comprised of a polyvinyl alcohol obtained by partial hydrolysis of polyvinyl acetate, or of a mixture of such polyvinyl alcohols.

5. The granules as claimed in claim 4, which further comprise
   - 0 to 80% by weight of a high-boiling solvent or solvent mixture,
   - 0 to 20% by weight of one or more wetting agents, and
   - 0 to 20% by weight of customary formulation adjuvants.

6. The granules as claimed in claim 4, which further comprise
   - 10 to 40% by weight of fenoxaprop-ethyl,
   - 20 to 60% by weight of a high-boiling solvent or solvent mixture,
   - 30 to 60% by weight of at least one polyvinyl alcohol obtained by partial hydrolysis of polyvinylacetate,
   - 0 to 20% by weight of one or more wetting agents, and
   - 5 to 15% by weight of customary formulation adjuvants.

7. The method of preparing aqueous preparations of pesticidally active substances, which method comprises mixing the granules as claimed in claim 1, together with customary formulation auxiliaries, to form aqueous preparations of pesticidally active substances.

* * * * *